United States Patent [19]

Hesse et al.

[11] Patent Number: 5,686,435
[45] Date of Patent: Nov. 11, 1997

[54] VITAMIN D AMIDE DERIVATIVES

[75] Inventors: Robert Henry Hesse, Winchester; Gaddam Subba Reddy, Lexington; Sundara Katugam Srinivasasetty Setty, Cambridge, all of Mass.

[73] Assignee: Research Institute for Medicine and Chemistry, Cambridge, Mass.

[21] Appl. No.: 568,755

[22] Filed: Dec. 7, 1995

Related U.S. Application Data

[63] Continuation of Ser. No. 211,722, May 31, 1994, Pat. No. 5,494,905.

[30] Foreign Application Priority Data

Nov. 7, 1991 [GB] United Kingdom ............... 91 23712.3
May 5, 1992 [GB] United Kingdom ............... 92 09658.5

[51] Int. Cl.$^6$ .......................... A61K 31/59; C07C 401/00
[52] U.S. Cl. ..................... 514/167; 514/169; 514/227.5; 514/237.5; 514/261; 514/319; 514/372; 514/374; 514/399; 514/406; 514/415; 514/423; 514/886; 544/59; 544/176; 544/264; 546/195; 546/205; 548/200; 548/214; 548/334.1; 548/341.5; 548/374.1; 548/361.1; 548/491; 548/530; 548/540; 548/579; 552/501; 552/544; 552/547; 552/505; 552/653; 564/188; 564/189
[58] Field of Search ..................... 552/501, 547, 552/544, 505, 653; 514/167, 169, 319, 227.5, 237.5, 261, 372, 374, 399, 406, 415, 423, 886; 564/189, 188; 544/59, 176, 264; 546/195, 205; 548/200, 214, 334.1, 341.5, 374.1, 361.1, 491, 530, 540, 579

[56] References Cited

U.S. PATENT DOCUMENTS

| 4,217,288 | 8/1980 | DeLuca et al. | 552/547 |
| 5,206,230 | 4/1993 | Ikekawa et al. | 514/167 |
| 5,494,905 | 2/1996 | Hesse et al. | 514/167 |

FOREIGN PATENT DOCUMENTS

A-2 021 115  11/1979  United Kingdom.

OTHER PUBLICATIONS

Yamada et al. J. Med. Chem., 1985, 28, 1148–1150.
Kabakoff et al.; *Archives Of Biochemistry And Biophysics*, vol. 221, No. 1, 1983, pp. 38–45.
Calverley, *Tetrahedron Letters*, vol. 43, No. 20, pp. 4609–4619, 1987.

*Primary Examiner*—Shailendra Kumar
*Attorney, Agent, or Firm*—Bacon & Thomas

[57] ABSTRACT

The invention pertains to vitamin D amide derivatives of formula (I). These novel 1α-hydroxy vitamin D derivatives and their 20-epi analogues comprise compounds of formula (I) and corresponding 5,6-trans isomers, where Y represents an alkylene or alkenylene group containing up to four carbon atoms; $R^1$ and $R^2$ independently represent a hydrogen atom or a lower alkyl or cycloalkyl group, or $R^1R^2N$— represents a heterocyclic group; and $R^3$ and $R^4$ independently represent a hydrogen atom or an O-protecting group. Active compounds, in which $R^3$ and $R^4$ are hydrogen atoms or metabolically labile O-protecting groups exhibit potent cell modulating effect, but minimal effect on calcium metabolism.

13 Claims, No Drawings

VITAMIN D AMIDE DERIVATIVES

This application is a continuation of application Ser. No. 08/211,722, filed May 31, 1994, now U.S. Pat. No. 5,494,905, which is a 371 of PCT/EP92/02577, Nov. 6, 1992.

This invention relates to novel vitamin D analogues, more particularly to 1a-hydroxy vitamin $D_3$ analogues having a modified side chain at the 17-position and exhibiting cell modulating activity.

Vitamin $D_3$, which has the formula

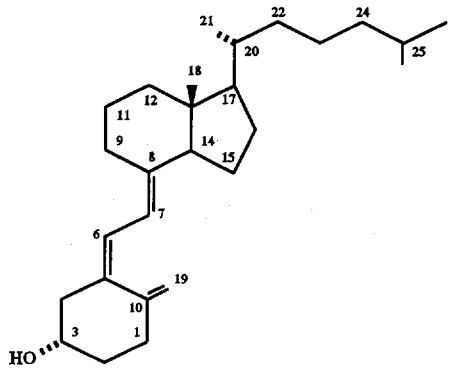

is well known to play a vital role in the metabolism of calcium, by promoting intestinal absorption of calcium and phosphorus, maintaining adequate serum levels of calcium and phosphorus and stimulating mobilisation of calcium from the bone fluid compartment in the presence of parathyroid hormone.

About 20 years ago it was learned that the D vitamins undergo hydroxylation in vivo, hydroxylation at the 25-position occurring in the liver and hydroxylation at the 1α-position occurring in the kidney, the resulting 1α,25-dihydroxy metabolite being the biologically active material. This discovery led to the synthesis of many analogues of vitamin D, evaluation of which indicated that hydroxyl groups at the 1α-position and at either the 24R- or the 25-position were essential for a compound or metabolite thereof to exhibit a substantial effect on calcium metabolism. While, as indicated above, such hydroxyl groups will normally ultimately be introduced in vivo, hydroxylation at the 24R- or 25-position occurring rather more readily than at the 1α-position, the use of vitamin D analogues already so hydroxylated has proved of substantial advantage by virtue of their enhanced levels of activity and their rapidity of action and subsequent elimination from the body. It will be appreciated that 1α-hydroxylated vitamin D derivatives are of especial benefit to patients suffering from renal failure.

Examples of hydroxylated vitamin D analogues in current use include the natural metabolite 1α,25-dihydroxy vitamin $D_3$ and 1α-hydroxy vitamin $D_3$ (which is readily 25-hydroxylated in vivo). Other reportedly promising compounds include 1α,24R-dihydroxy vitamin $D_3$, $D_2$ analogues of the above compounds and 1α,25-dihydroxy analogues carrying fluorine atoms at the 24-, 26- and/or 27-positions (see De Luca and Schnoes, Ann. Rev. Biochem. (1983), 52, pp 411–439 and De Luca et al., Top. Curr. Chem. (1979), 83, pp 1–65).

More recently it has been learned that the natural metabolite 1α,25-dihydroxy vitamin $D_3$ has additional effects on cellular metabolism. These cell modulating effects include stimulation of cell maturation and differentiation (Tanaka et al., Biochem. J. (1982), 204, pp 713–719; Amento et al., J. Clin. Invest. (1984), 73, pp 731–739; Colston et al., Endocrinology (1981), 108, pp 1083–1086; Abe et al., Proc. Nat. Acad. Sci. (1981), 78, pp 4990–4994) and immunosuppressive effects (e.g. inhibition of interleukin II production) (Rigby, Immunology Today (1988), 9, pp 54–58). Still more recently, an immunopotentiating effect of 1α,25-dihydroxy vitamin $D_3$ has been observed, the compound having been found to stimulate the production of bactericidal oxygen metabolites and the chemotactic response of leukocytes (see, for example, Cohen et al., J. Immunol. (1986), 136, pp 1049–1053). It is well known that leukocytes play a major role in the body's defence against various infections (see, for example, Roitt, Brostoff and Male, "Immunology" $2^{nd}$ Ed. (1989), C. V. Mosby, St. Louis, sec 16.10–16.13 and 17.4–17.5), e.g. by adhering to and engulfing invading organisms (chemotactic response) and/or by producing superoxides and/or other toxic oxygen metabolites. It is known that this response may also be stimulated by mitogens such as the co-carcinogenic phorbal esters and γ-interferon, which are structurally quite different from vitamin D analogues.

By virtue of these effects on cellular metabolism, 1α,25-dihydroxy vitamin $D_3$ in principle has therapeutic potential in such diverse areas as treatment of psoriasis, inflammatory and autoimmune diseases, neoplasias and hyperplasias, as an adjunct in the chemotherapy of infections (inter alia bacterial, viral and fungal), and in other therapeutic modalities in which mononuclear phagocytes are involved. 1α,25-dihydroxy vitamin $D_3$ and 1α-hydroxy vitamin $D_3$ have also been proposed for use in the treatment of hypertension (Lind et al., Acta Med. Scand. (1987), 222, pp 423–427) and diabetes mellitus (Inomata et al., Bone Mineral (1986), 1, pp 187–192), and it has been suggested that 1α,25-dihydroxy vitamin $D_3$ may promote hair growth (Lancet, 4 Mar. 1989, p 478) and may be useful in the treatment of acne (Malloy et al., Tricontinental Meeting for Investigative Dermatology, Washington, 1989). However, the potent effects of 1α,25-dihydroxy vitamin $D_3$ and 1α-hydroxy vitamin $D_3$ on calcium metabolism will normally preclude such uses, since dosages at a level sufficient to elicit a desired cell modulating, immunosuppressive or immunopotentiating effect tend to lead to unacceptable hypercalcaemia. This has led to attempts to synthesize new analogues having reduced effects on calcium metabolism but which still exhibit the desired effects on cellular metabolism.

There have been reports of new analogues which exhibit, to at least a moderate degree, this desired separation of activity. Thus the compound MC-903, which is a 22,23-unsaturated 1α,24R-dihydroxy vitamin $D_3$ analogue carrying a cyclopropyl group at the 24-position instead of the usual $C_{25}$–$C_{27}$ configuration of the cholestane side chain, and which is under clinical trial for the treatment of psoriasis, is reported to exhibit an effect on cell maturation comparable in magnitude to 1α,25-dihydroxy vitamin $D_3$, while exhibiting a smaller hypercalcaemic effect (Calverley, Tetrahedron (1987), 43, pp 4609–4619; and Holick, Arch. Dermatol. (1989), 125, pp 1692–1696). Similar claims have been made for analogues of 1α,25-dihydroxy vitamin $D_3$, e.g. the 22-oxa (Abe et al., Endocrinology (1989), 124, pp 2645–2647), the 24- and the 26- homo (Ostrem et al., J. Biol. Chem. (1987), 262, pp 14164–14171), the 16-dehydro-23,24-ethynyl (Zhou et al., Blood (1989), 74, pp 82–93) and the 19-nor-10-dihydro (Perlman et al., Tetrahedron Lett. (1990), pp 1823–1824).

It does not appear possible to deduce from these disclosures either which compounds will exhibit cell modulating activity(or the level of any such activity) or to determine factors which lead to a separation of activities as regards cell modulation and calcium metabolism. Thus while the majority of results suggest that the presence of a hydroxyl group towards the end of a cholestane-type side chain or homologue thereof is necessary for compounds to show significant cell modulating activity, the findings of Ostrem et al. (op. cit.) indicate that analogues having only a short, unsubstituted 17-position side chain (e.g. isopropyl or sec-butyl, as in homo- or bis-homo-pregnanes) exhibit quite substantial differentiation-inducing activity and are more potent than corresponding short side chain compounds bearing a side chain hydroxyl group. While a number of these compounds appear to show cell modulating activity at a similar level to that of 1α,25-dihydroxy vitamin $D_3$, they also appear still to show appreciable effects on calcium metabolism, such activity being attenuated by at most two orders of magnitude relative to that of 1α,25-dihydroxy vitamin $D_3$. This may therefore give rise to cumulative toxicity problems if such compounds are used in long term therapy, particularly where systemic application is required, e.g. for treatment of inflammatory and autoimmune diseases, neoplasias and hyperplasias, or in oral therapy for treatment of psoriasis.

The present invention is based on the surprising discovery of a number of 1α-hydroxy vitamin D derivatives and 20-epi analogues thereof in which the 17-position side chain terminates in an optionally N-substituted or N,N-disubstituted carbamoyl group, which derivatives, while exhibiting minimal effect on calcium metabolism, may have a potent cell modulating effect, for example as evidenced by eliciting cell differentiation and maturation, inhibiting proliferation and/ or by activating monocytes (e.g. as estimated by the method of Styrt et al., Blood (1986), 67, pp 334–342). Thus compounds according to the invention have been found to have insignificant effects on serum calcium and phosphorus levels in rats, even when administered in amounts of 100 times a conventional dosage for 1α,25-dihydroxy vitamin $D_3$. The compounds accordingly exhibit an advantageous therapeutic ratio of cell modulating to calcemic activity.

A further advantage of the compounds of the invention is that they have a very low affinity for the intestinal 1α,25-dihydroxycholecalciferol receptor.

The invention includes compounds of formulae (I) and (II)

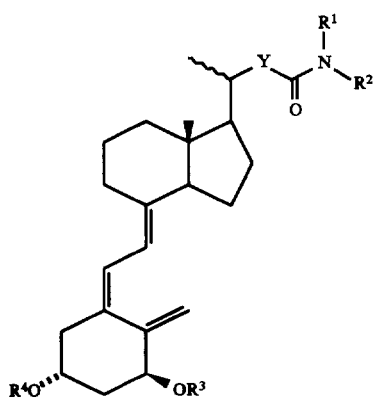
(I)

-continued

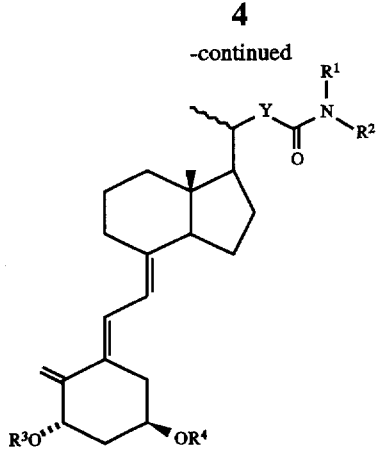
(II)

(where Y represents an alkylene or alkenylene group containing up to 4 carbon atoms; $R^1$ and $R^2$, which may be the same or different, each represent a hydrogen atom or a lower alkyl or cycloalkyl group or, together with the nitrogen atom to which they are attached, form a heterocyclic group; and $R^3$ and $R^4$, which may be the same or different, each represents a hydrogen atom or an O-protecting group).

It will be appreciated that formulae (I) and (II) embrace compounds having the 20R configuration of natural vitamin D derivatives, compounds having the 20S configuration of epi-vitamin D derivatives, and mixtures of the two isomers. The formulae also include active compounds in which $R^3$ and $R^4$ represent hydrogen atoms and precursors therefor in which $R^3$ and $R^4$ are O-protecting groups, although such precursors may themselves be active where the O-protecting group or groups are metabolically labile.

The fact that active compounds (I) and (II), which possess sizeable vitamin D-like 17-position side chains which do not carry a 24- or 25- hydroxyl group and which in many cases are not capable of being hydroxylated at these positions, exhibit cell modulating activity is unexpected in the light of previous findings in this area, which strongly suggest the necessity of such a hydroxyl group. The observation of useful cell modulating activity for active compounds of formulae (I) and (II) is even more surprising in view of a report that compounds having a similar side chain but lacking a 1α-hydroxyl group are without vitamin D-like activity and are in fact useful as antagonists of vitamin D, apparently by virtue of blocking 25-hydroxylation (see U.S. Pat. No. 4,217,288).

It has also been noted (Serensen et al., Biochemical Pharmacology (1990), 39, pp 391–393) that the above-mentioned 1α,24R-dihydroxy vitamin $D_3$ analogue MC-903 is oxidised in vivo to the corresponding 24-oxo compound, and that this metabolite shows considerably reduced activity as regards effects on cell proliferation and differentiation compared to MC-903. This suggests that introduction of a 24-oxo group comprises a deactivation step in respect of cell modulating activity, in contrast to our findings concerning the 24-oxo and homologous compounds of the present invention.

Furthermore, for the reasons outlined above, the observed separation of cell modulating and calcemic activities exhibited by the active compounds of the invention could not have been predicted from prior art relating to vitamin D analogues exhibiting cell modulating activity.

The active 5,6-trans (5E) isomers of formula (II), while being about one order of magnitude less active than the active 5,6-cis (5Z) isomers of formula (I) as regards cell modulating activity, are also less active in elevating serum calcium levels and thus again exhibit an appreciable and unexpected separation of cell modulating and calcemic activities.

The group Y in the above formulae may contain 0, 1 or 2 double bonds and may, for example, be of the formula —(R$^4$)$_m$—(R$^8$)$_n$— where R$^4$ is —CH=CH—, R$^8$ is —CH$_2$—, m is 0, 1 or 2 and n is zero or an integer such that 2m+n=1, 2, 3 or 4. Y may advantageously be a C$_{2-4}$ alkylene group.

Where R$^1$ and/or R$^2$ in formulae (I) and (II) represent lower alkyl groups these may, for example, be C$_{1-6}$ alkyl groups such as methyl, ethyl, propyl and butyl groups. Lower cycloalkyl groups may, for example, contain 3–8 carbon atoms, e.g. as in cyclopropyl, cyclopentyl and cyclohexyl groups. Where the group R$^1$R$^2$N— represents a heterocyclic group this may, for example, contain one or more further heteroatoms selected from O, N and S and may comprise one or more rings, e.g. each having 5 or 6 ring members, for example as in N-attached pyrrolyl, pyrazolyl, imidazolyl, indolyl, indazolyl, purinyl, pyrrolidinyl, imidazolidinyl, pyrazolidinyl, piperidinyl, morpholino, thiazolidinyl or thiamorpholino groups.

Where R$^3$ and R$^4$ represent O-protecting groups these may, for example, be cleavable O-protecting groups such as are commonly known in the art. Suitable groups include etherifying groups such as silyl groups (e.g. tri (lower alkyl) silyl groups such as trimethylsilyl, triethylsilyl, triisopropylsilyl or t-butyldimethylsilyl; tri (aryl) silyl groups such as triphenylsilyl; and mixed alkyl-arylsilyl groups); lower (e.g. C$_{1-6}$) alkyl groups optionally interrupted by an oxygen atom, such as methyl, methoxymethyl or methoxyethoxymethyl; and cyclic groups such as tetrahydropyranyl. Esterifying O-protecting groups include lower (e.g. C$_{1-6}$) alkanoyl such as acetyl, propionyl, isobutyryl or pivaloyl; aroyl (e.g. containing 7–15 carbon atoms) such as benzoyl or 4-phenylazobenzoyl; lower alkane sulphonyl such as (optionally halogenated) methane sulphonyl; and arene sulphonyl such as p-toluene sulphonyl. Such O-protected derivatives are useful as intermediates in the preparation of active 1α,3β-diols of formulae (I) and (II) where R$^3$ and R$^4$ represent hydrogen atoms, although, as indicated above, where the O-protecting groups are metabolically labile in vivo, such ethers and esters of formulae (I) and (II) may be used directly in therapy.

The cell modulating activity of active compounds according to the invention, combined with their substantial lack of calcaemic effect, render them of interest (both alone and as adjuncts) in the management of neoplastic disease, particularly myelogenous leukemias. They may also be used either alone or as adjuncts in the chemotherapy of infection and in all other therapeutic modalities in which mononuclear phagocytes are involved, for example in treatment of bone disease (e.g. osteoporosis), autoimmune diseases, host-graft reaction, transplant rejection, and inflammatory diseases, neoplasias and hyperplasias such as psoriasis. Acne, alopecia, skin aging (including photoaging), hypertension, rheumatoid arthritis and asthma are other conditions which may be treated with active compounds according to the invention; the invention embraces use of these compounds in the therapy or prophylaxis of such conditions and in the manufacture of medicaments for such treatment or prophylaxis.

We believe that the active 20R isomers of formulae (I) and (II) may be preferred for treatment of infections, e.g. in combination therapy, whereas the active 20S epi-isomers may be preferred for applications involving an immunosuppressive effect, e.g. in treatment of autoimmune and inflammatory diseases, rheumatoid arthritis, asthma etc. This view is supported by, for example, the work of Binderup et al. concerning 20-epi-vitamin D$_3$ analogues reported in *Biochemical Pharmacology* (1991), 42(8), pp 1569-1575.

Active compounds according to the invention may be formulated for administration by any convenient route, e.g. orally (including sublingually), parenterally, rectally or by inhalation; pharmaceutical compositions so formulated comprise a feature of the invention.

Orally administrable compositions may, if desired, contain one or more physiologically compatible carriers and/or excipients and may be solid or liquid. The compositions may take any convenient form including, for example, tablets, coated tablets, capsules, lozenges, aqueous or oily suspensions, solutions, emulsions, syrups, elixirs and dry products suitable for reconstitution with water or another suitable liquid vehicle before use. The compositions may advantageously be prepared in dosage unit form. Tablets and capsules according to the invention may, if desired, contain conventional ingredients such as binding agents, for example syrup, acacia, gelatin, sorbitol, tragacanth or polyvinyl-pyrollidone; fillers, for example lactose, sugar, maize-starch, calcium phosphate, sorbitol or glycine; lubricants, for example magnesium stearate, talc, polyethylene glycol or silica; disintegrants, for example potato starch; or acceptable wetting agents such as sodium lauryl sulphate. Tablets may be coated according to methods well known in the art.

Liquid compositions may contain conventional additives such as suspending agents, for example sorbitol syrup, methyl cellulose, glucose/sugar syrup, gelatin, hydroxymethylcellulose, carboxymethylcellulose, aluminium stearate gel or hydrogenated edible fats; emulsifying agents, for example lecithin, sorbitan monooleate or acacia; non-aqueous vehicles, which may include edible oils, for example vegetable oils such as arachis oil, almond oil, fractionated coconut oil, fish-liver oils, oily esters such as polysorbate 80, propylene glycol, or ethyl alcohol; and preservatives, for example methyl or propyl p-hydroxybenzoates or sorbic acid. Liquid compositions may conveniently be encapsulated in, for example, gelatin to give a product in dosage unit form.

Compositions for parenteral administration may be formulated using an injectable liquid carrier such as sterile pyrogen-free water, sterile peroxide-free ethyl oleate, dehydrated alcohol or propylene glycol or a dehydrated alcohol/propylene glycol mixture, and may be injected intravenously, intraperitoneally or intramuscularly.

Compositions for rectal administration may be formulated using a conventional suppository base such as cocoa butter or another glyceride.

Compositions for administration by inhalation are conveniently formulated for self-propelled delivery, e.g. in metered dose form, for example as a suspension in a propellant such as a halogenated hydrocarbon filled into an aerosol container provided with a metering dispense valve.

It may be advantageous to incorporate an antioxidant, for example ascorbic acid, butylated hydroxyanisole or hydroquinone in the compositions of the invention to enhance their storage life.

Where any of the above compositions are prepared in dosage unit form these may for example contain 0.05–250 µg, e.g. 0.1–50 µg, of active compound according to the invention per unit dosage form. The compositions may if desired incorporate one or more further active ingredients.

A suitable daily dose of an active compound according to the invention may for example be in the range 0.1–500 µg, e.g. 0.2–100 µg, per day, depending on factors such as the severity of the condition being treated and the age, weight and condition of the subject.

Compounds according to the invention may be prepared by the following methods:

A) Compounds of formula (I) may be prepared by isomerisation of a corresponding 5,6-trans compound of formula (II), followed if necessary and/or desired by removal of any O-protecting groups. Isomerisation may be effected by, for example, treatment with iodine, with a disulphide or diselenide, or by irradiation with ultraviolet light, preferably in the presence of a triplet sensitiser. 1α-Hydroxy compounds of formula (II) may themselves be prepared by oxidising a corresponding 1-unsubstituted 5,6-trans compound using a selenite ester or selenium dioxide or selenous acid in the presence of an alcohol, e.g. as described in GB-A-2038834, the contents of which are incorporated herein by reference. The 1-unsubstituted 5,6-trans compound may, if desired, be prepared by in situ isomerisation of the corresponding 5,6-cis vitamin derivative under the conditions of the oxidation.

B) Compounds of formulae (I) or (II) may be prepared by reaction of a compound of formula (III)

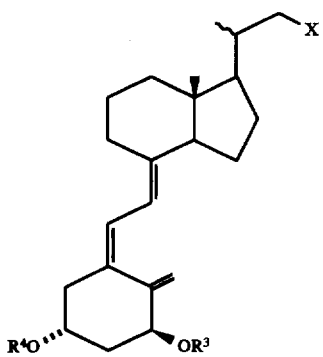
(III)

(where $R^3$ and $R^4$ are as hereinbefore defined and X represents an oxo or phosphoranylidene group; a metallated silane or sulphone group; a group —$(CH_2)_a$L where a is 0, 1 or 2 and L represents a leaving group, e.g. a sulphonate ester group such as lower alkyl sulphonyloxy, lower fluoroalkyl sulphonyloxy or aryl sulphonyloxy or, more preferably, a halogen atom such as chlorine, bromine or iodine; or a group —$(CH_2)_b R^5$ where b is 0, 1, 2 or 3 and $R^5$ represents a cyano group or an esterified carboxyl or thiocarboxyl group such as an alkoxycarbonyl, aralkoxycarbonyl, aryloxycarbonyl, alkylthiocarbonyl, aralkylthiocarbonyl or arylthiocarbonyl group) or a corresponding 5,6-trans compound, with one or more reagents serving to generate the desired side chain amide grouping, followed where necessary and/or desired by removal of any O-protecting groups. It will be appreciated that a compound of formula (II) obtained in this way may if desired be converted to a compound of formula (I) by isomerisation as described in process (A).

Reactions according to process (B) which may be used to prepare compounds of formula (I) or (II) in which Y represents an alkylene group include:

B1) Reaction of a compound (III) in which X represents a group —$(CH_2)_a$L as hereinbefore defined, or a 5,6-trans isomer thereof, with a metallated or dimetallated salt of an amide of formula (IV)

$$CH_3\text{-CO-}NR^1R^2 \quad \quad (IV)$$

(where $R^1$ and $R^2$ are as hereinbefore defined), e.g. an alkali metal salt such as a lithium salt prepared by reaction with a base such as lithium diisopropylamide.

B2) Reaction of a compound (III) in which X represents a group —$(CH_2)_b R^5$ as hereinbefore defined, or a corresponding 5,6-trans isomer, to convert the ester, thioester or cyano group $R^5$ to the desired amide group, e.g. by direct aminolysis of an ester or thioester or indirectly via the corresponding free acid obtained by hydrolysis of the ester, thioester or nitrile or via an acid halide obtained therefrom. It will be appreciated that nitriles of formula (III) may be partially hydrolysed directly to compounds (I) in which $R^1$ and $R^2$ are both hydrogen atoms.

B3) Reaction of a compound (III) in which X represents a group —$(CH_2)_a$L as hereinbefore defined, or a 5,6-trans isomer thereof, with a reagent serving to introduce a one-carbon fragment (e.g. a metal cyanide or metallated trithiane) and conversion of the group so introduced to the desired —$CONR^1R^2$ group, e.g. as described for process (B2).

Reaction according to process (B) which may be used to prepare compounds of formula (I) or (II) in which Y represents an alkenylene group include:

B4) Reaction of a compound (III) in which X represents an oxo group, or a 5,6-trans isomer thereof, according to a Wittig type reaction, for example with a phosphorane of formula $$(R^C)_3P=CH-(Y^1)_p-R^D \quad \quad (V)$$

(where $Y^1$ is an alkylene or alkenylene group having up to 2 carbon atoms; p is 0 or 1; $R^C$ is a hydrocarbyl group, e.g. an alkyl or aralkyl group or an aryl group such as phenyl; and $R^D$ is an aminocarbonyl group —$CONR^1R^2$ as defined above, or a precursor group convertible thereto, such as an ester, thioester or cyano group), followed, where necessary, by conversion to generate the group —$CONR^1R^2$. Alternatively the phosphorane (V) may be replaced by a metallated silane $(R^C)_3Si-CHM-(Y^1)_p-R^D$ or by a metallated sulphone $R^C SO_2-CHM-(Y^1)_p-R^D$ (where $R^C$, $R^D$, $Y^1$ and p have the above meanings and M is a metal atom, e.g. an alkali metal such as lithium or sodium), this latter reaction being followed by reduction of the intermediate hydroxysulphone to form the required double bond, e.g. using sodium amalgam. Conversely these reaction may be effected using a compound of formula (III) in which X is a phosphoranylidene grouping =$P(R^C)_3$ or a corresponding metallated derivative of formula (III) in which X is —$Si(R^C)_3$ or —$SO_2R^C$, (where $R^C$ has the above meaning) with an aldehyde of the formula HCO—$(Y^1)_p$—$R^D$ (where p, $R^D$ and $Y^1$ have the above meanings).

Compounds of formula (III) having the normal 20-position configuration of natural vitamin D derivatives, i.e. compounds of formula (IIIa)

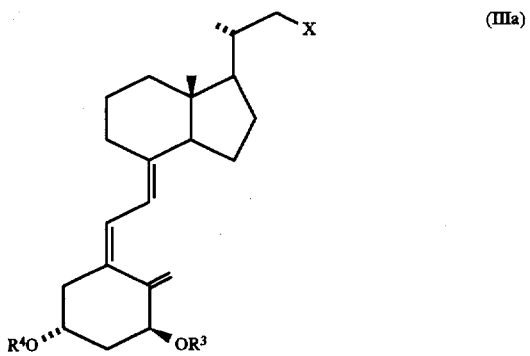
(IIIa)

and/or 5,6-trans isomers thereof may be prepared from 1α-hydroxy vitamin $D_2$ or an O-protected derivative thereof by oxidative cleavage of the 22,23-double bond, the vitamin D₂ compound preferably being stabilised by formation of a Diels Alder dienophile adduct, e.g. with sulphur dioxide or a diacylazo compound, as described in GB-A-2114570 (the contents of which are incorporated herein by reference). In this way a 20S compound (IIIa) in which X represents an oxo group may be obtained.

Such compounds (IIIa) or, more preferably, their dienophile adducts may be isomerised by, for example, treatment with a mild base, e.g. an inorganic base such as sodium bicarbonate or a tertiary organic base such as DABCO (i.e. 1,4-diazabicyclo[2.2.2]octane) or DBU (i.e. 1,8-diazabicyclo[5.4.0]undec-7-ene), to yield a mixture of 20R and 20S isomers from which the pure 20R epi-isomer, i.e. a compound of formula (IIIb)

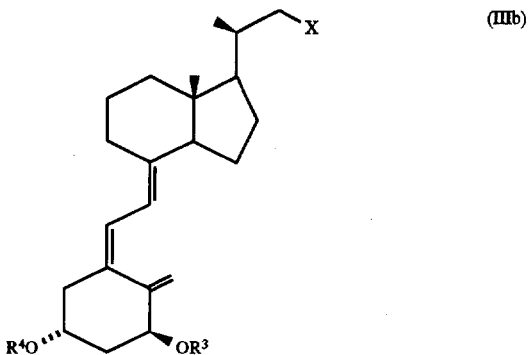

(in which X represents an oxo group) or a dienophile adduct thereof may be isolated chromatographically (e.g. as described by Calverley in Tetrahedron (1987), 43, pp 4609-4619). Alternatively, separation of a desired epi-isomer may be delayed until a later stage in the synthesis, up to and including the final step.

The oxo group X in thus-obtained compounds (IIIa) and (IIIb) or mixtures thereof may be converted by reduction to a hydroxyl group and thence to compounds in which X represents a group —(CH₂)ₐL where a=0 and L is a halogen atom by, for example, conversion to a sulphonate ester (e.g. a tosylate) and nucleophilic displacement of the tosylate group by reaction with a halide salt (e.g. an alkali metal bromide). These last compounds (III) and 5,6-trans isomers thereof may be reacted with, for example, a metal cyanide as described for process (B3) to generate a compound (III) or 5,6-trans isomer thereof in which X represents a group —(CH₂)ᵦR⁵ where b=0; the cyano group R⁵ may if desired subsequently be modified by hydrolysis and esterification.

Compounds (III) and corresponding 5,6-trans isomers in which X represents a group —(CH₂)ᵦR⁵ where b is 1 or 2 and R⁵ is as hereinbefore defined may be prepared by reaction of a compound (III) or a 5,6-trans isomer thereof wherein X represents a group —(CH₂)ₐL where a is 0 or 1 and L is as hereinbefore defined with a metallated derivative of an ester or thioester of acetic acid, with a derivative containing another carbanionic equivalent of acetic acid (e.g. a metallated derivative of acetonitrile), or with a metallated malonate ester. In this last instance the reaction product is partially hydrolysed to yield a monoester which may be decarboxylated by heating to yield a compound (III) in which X is a group —(CH₂)ᵦR⁵ where R⁵ is an ester group.

Compounds (III) and corresponding 5,6-trans isomers in which X represents a group —(CH₂)ₐL in which a is 1 or 2 and L is as hereinbefore defined may be prepared from compounds (III) or 5,6-trans isomers thereof where X represents a group —(CH₂)ᵦR⁵ in which b is 0 or 1 and R⁵ is an ester group by reducing the ester to an alcohol, e.g. using lithium aluminium hydride, and converting the hydroxyl group to a leaving group, e.g. as hereinbefore described.

1-Unsubstituted analogues of compounds of formula (III) and/or 5,6-trans isomers thereof may also be prepared in similar manner from vitamin D₂, and then reacted so as to generate the desired side chain amide group and subjected to 1α-hydroxylation, e.g. as described in the above-mentioned GB-A-2038834, at an appropriate stage of the synthesis.

In general, either 5,6-cis or 5,6-trans geometry may be present at any step, although it may be preferred to employ 5,6-trans isomers in the above-mentioned 1α-hydroxylation and 22,23-double bond oxidative cleavage reactions. Conversion of 5,6-trans geometry to 5,6-cis is thus most advantageously effected after introduction of the 1α-hydroxyl group.

O-protecting groups present at the 1α- and/or 3β-positions may be removed by, for example, conventional methods such as are well documented in the literature. Thus esterifying acyl groups may be removed by basic hydrolysis, e.g. using an alkali metal alkoxide in an alkanol. Etherifying groups such as silyl groups may be removed by acid hydrolysis or treatment with tetraalkyl ammonium fluorides. The use of such acid-labile but base-stable protecting groups may be of advantage when reacting compounds of formula (III) and corresponding 5,6-trans isomers and/or 1-unsubstituted compounds, in view of the strongly basic conditions normally employed in the homologation steps used to build up the desired side chain.

The following non-limitative examples serve to illustrate the invention. All temperatures are in °C.

EXAMPLE 1 a) 1α,3β-Di(triisopropylsilyloxy)-9,10-seco-25-azacholesta-5(E),7,10(19)-trien-24-one [Formula (II) - 20R isomer, R¹=R²=CH₃, R³=R⁴=(i-Pr)₃Si, Y=—CH₂CH₂—]

1α,3β-Di(triisopropylsilyloxy)-9,10-seco-20-p-toluenesulphonyloxymethylpregna-5(E),7,10(19)-triene [5,6-trans isomer of Formula (IIIa) - R³=R⁴=(i-Pr)₃Si, X=tosyloxy- NMR δ 7.5 (2H, d,j=8, aryl), 7.03 (2H, d, j=8, aryl), 6.16 & 5.6 (AB, j=11, 6H, 7H), 4.8 (2H, s, 19H), 4.46 (1H, t, j=11, 1H), 4.33 to 3.5 (3H, m, 3H, 22H's), 2.36 (3H, s, aryl CH₃), 0.5 (3H, s, 18H's)] (710 mg) was heated under reflux in acetonitrile (8 ml) containing excess lithium bromide (620 mg). After 45 minutes the mixture was cooled, diluted with water, and extracted with ether. The ether extract was purified by chromatography on silica gel to give 490 mg of the corresponding 20-bromomethyl compound [NMR δ 6.25 & 5.66 (ABq, j=11, 6,7H's), 4.83 (2H, s, 19H's), 4.66 to 4.0 (2H, m, 1,3H's), 3.31 (2H, bs, 22H's), 0.55 (3H, s, 18H's). UV λ_max 270(21300), λ_min 229 (4922)]. A solution of this compound (245 mg) in hexamethylphosphoramide (0.7 ml) was added at −78° C. to a solution of the lithium salt of N,N-dimethylacetamide [prepared from N,N-dimethylacetamide (0.158 ml) and lithium diisopropylamide (1.54 mmole) in tetrahydrofuran (4.6 ml)]. The reaction mixture was allowed to warm to room temperature (30 minutes), stirred for a further 2 hours, then treated with saturated aqueous ammonium chloride followed by water, and the product was extracted with ether. Purification by chromatography afforded the title compound (208 mg). NMR δ 6.4 & 5.76 (ABq, j=11, 6,7H's), 4.93 (2H, s, 19H's), 4.76 to 4.01 (2H, m, 1,3H's), 3.31 & 2.9 (each 3H, s, N-CH₃), 0.55 (3H, s, 18H's). IR ν_max(CDCl₃) 1625 cm⁻¹ (amide). UV ν_max 270 (23333), λ_min 230 (7337).

b) 1α,3β-Dihydroxy-9,10-seco-25-azacholesta-5(Z),7,10 (19)-trien-24-one [Formula (I) - 20R isomer, R¹=R²=CH₃, R³=R⁴=H, Y=—CH₂CH₂—]

The product of (a) above was irradiated for 45 minutes in benzene (6 ml) containing phenazine (12 mg). The solvent was then removed and the crude 5Z compound treated at room temperature for 2 hours with aqueous tetrabutylammonium fluoride (0.3 ml, 1M) in tetrahydrofuran (1 ml). Dilution with water, extraction of the product into ether, and purification by preparative TLC afforded the title compound (21 mg). NMR δ 6.36 & 5.98 (ABq, j=11, 6,7H's), 5.26 & 4.95 (each 1H, s, 19H's), 4.63 to 3.9 (2H, m, 1,3H's), 3.0 & 2.93 (each 3H, s, N-CH$_3$), 0.56 (3H, s, 18H's). IR $v_{max}$ (CDCl$_3$) 3610 & 3410 (OH), 1630 cm$^{-1}$ (amide). UV $\lambda_{max}$ 265 (18,300), $\lambda_{min}$ 228 (10166).

EXAMPLE 2 a) 3β-Hydroxy-20-(2-ethoxycarbonylethyl)-9,10-sesopregna-5(E),7,10(19)-triene [1-unsubstituted analogue of 5,6-trans isomer of Formula (IIIa) - R$^4$=H, X=CH$_2$CO.O.C$_2$H$_5$]

The sulphur dioxide adduct of 3β-acetoxy-20-hydroxymethyl-9,10-secopregna-5(E),7,10(19)-triene (4.54 g) was dissolved in dichloromethane (40 ml) containing 1,8-bis(dimethylamino)naphthalene (3.34 g) and treated at −30° C. with triflouromethane sulphonic anhydride (3.812 g). The reaction mixture was stirred briefly, allowed to warm to room temperature, cooled to −30° C., then treated with a solution of sodio-diethyl malonate [prepared from diethyl malonate (8.32 g) and sodium hydride (1.248 g)] in tetrahydrofuran (40 ml). The mixture was allowed to warm to room temperature and stirred for 15 minutes. Addition of saturated aqueous ammonium chloride, then water, extraction of the product into ether and purification by chromatography afforded the sulphur dioxide adduct of 3β-acetoxy-20(2,2-diethoxycarbonylethyl)-9,10-secopregna-5(E),7,10(19)-triene as a mixture of 6R and 6S compounds (4.675 g) [NMR δ 5.1 to 4.26 (3H, m, 3,6,7H's), 4.0 (4H, q, j=7, O—CH$_2$Me), 3.46 (2H, bs, 19H's), 1.93 & 1.90 (total 3H, each s, acetylH's), 0.63 & 0.56 (total of 3H, s, 18H's)].

A solution of this product (4.475 g) in ethanol (15 ml) was treated with ethanolic potassium hydroxide (20 ml, 1M) and water (0.380 ml). The mixture was stirred at room temperature for 1.5 hours, then diluted with water and acidified, and the product was extracted into ether. The crude mono ester thus obtained was decarboxylated (and sulphur dioxide removed to regenerate the 5, 7, 10 (19)-triene system) by heating at 125° in dimethyl sulphoxide (15 ml) containing sodium bicarbonate (5 g) for 20 minutes. The mixture was cooled, then diluted with water, and the product was extracted into ether and purified by chromatography to give the title compound (2.22 g). NMR δ 6.16 & 5.56 (ABq, j=11, 6,7H's), 4.53 & 4.43 (each 1H, s, 19H's), 3.91 (2H, q, j=7, O—CH$_2$Me), 0.56 (3H, s, 18H's). UV $\lambda_{max}$ 272 (23600), $\lambda_{min}$ 231 (5645).

b) 1α,3β-Di(triisopropylsilyloxy)-20-(2-ethoxycarbonylethyl)-9,10-secopregna-5(E),7,10(19)-triene [5,6-trans isomer of Formula (IIIa) - R$^3$=R$^4$=(i-Pr)$_3$Si, X=CH$_2$CO.O.C$_2$H$_5$]

The product from (a) above (2.568 g) was reacted with triisopropylsilyl chloride (1.214 g) and imidazole (1.42 g) in dichloromethane (5 ml) to convert the 3β-hydroxyl group to a triisopropylsilyloxy group. This product, in 1,2-dichloroethane (32 ml) was hydroxylated by treatment with selenium dioxide (0.51 g) in acetonitrile (32 ml) and N-methylmorpholine N-oxide (2.47 g) in dichloromethane (32 ml) according to the process of GB-A-2038834 to give (after purification by chromatography) the 1α-hydroxy compound (1.37 g) [NMR δ 6.3 & 5.7 (ABq, j=11, 6,7H's), 4.9 & 4.8 (each 1H, s, 19H's), 4.63 to 3.7 (2H, m, 1,3H's), 4.0 (2H, q, j=7, O—CH$_2$Me), 0.56 (3H, s, 18H's). UV $\lambda_{max}$ 270 (23,200), $\lambda_{min}$ 229 (5068)]. This product was silylated as described above to give the title compound (1.575 g). NMR δ 6.26 & 5.68 (ABq, j=11, 6,7H's), 4.86 (2H, s, 19H's), 4.73 to 3.73 (2H, m, 1,3H's), 4.0 (2H, q, j=7, O—CH$_2$Me), 0.53 (3H, s, 18H's). UV $\lambda_{max}$ 270 (23600), $\lambda_{min}$ 228 (5053).

c) 1α,3β-Di(triisopropylsilyloxy)-25,26,27-trinor-9,10-secocholesta-5(E),7,10(19)-trien-24-ol[5,6-trans isomer of Formula (IIIa) - R$^3$=R$^4$=(i-Pr)$_3$Si, X=CH$_2$CH$_2$OH]

A solution of the product from (b) above (350 mg) in ether (1 ml) was added to a stirred solution of lithium aluminium hydride (100 mg) in ether (5 ml) at 0°. The mixture was stirred at room temperature for 0.5 hours, cooled to 0°, treated with aqueous sodium sulphate and the product extracted into ether. The ether was washed with water then brine, and was removed in vacuo to give the title compound. NMR δ (CCl$_4$): 6.21 & 5.63 (ABQ, 6 and 7H's); 4.82 (s, 2H, 19 H's); 4.66–3.98 (2H, m, t, 3 H's); 3.41 (bs, 2H, 24 H's); 0.55 (s, 3H, 18 Me). UV (Et$_2$O): $\lambda_{max}$ 270 (23,600); $\lambda_{min}$ 229 (5,714).

d) 1α,3β-Di(triisopropylsilyloxy)-25,26,27-trinor-9,10-secocholesta-5(E),7,10(19)-trien-24-bromide [5,6-trans isomer of Formula (IIIa) - R$^3$=R$^4$=(i-Pr)$_3$Si, X=CH$_2$CH$_2$Br]

A solution of the alcohol from (c) above (330 mg) in dichoromethane (4 ml) containing 1,8-bis(dimethylamino) naphthalene (309 mg) was treated for 3 minutes at −40° with trifluromethane sulphonic anhydride (0.203 g). The mixture was then treated with a solution of sodium bromide (1.03 g) and tetrabutylammonium bromide (0.01 g) in water (5 ml) and allowed to warm to room temperature. After 30 minutes, the reaction mixture was partitioned between dichloromethane and water. The organic phase was isolated, washed with dilute sulphuric acid, concentrated and the product purified by chromatography to give 0.26 g of the title compound. NMR δ (CCl$_4$): 6.06 & 5.6 (ABQ, 6, 7 H's); 4.71 (s, 2H, 19 H's); 4.63–4.0 (m, 2H, 1, 3 H's); 3.21 (t, 2H, 24 H's); 0.56 (s, 3H, 18 Me). UV (Et$_2$O): $\lambda_{max}$ 270 (23,600); $\lambda_{min}$ 229 (6098).

e) 1α,3β-Di(triisopropylsilyloxy)-23,23-bisbomo-24-aza-9,10-secocholesta-5(E), 7,10(19)-trien-24-one [Formula (II) - 20R isomer, R$^1$=R$_2$=CH$_3$, R$^3$=R$^4$=(i-Pr)$_3$Si, Y=—CH$_2$CH$_2$CH$_2$CH$_2$—]

The bromide from (d) above (0.18 g) in hexamethylphosphoramide (0.8 ml) was treated with the lithium salt of N,N-dimethylacetamide as described in Example 1 (a) to give the title compound (0.103 g). NMR δ (CCl$_4$): 6.26 & 5.66 (ABQ, 6, 7 H's); 4.83 (s, 2H, 19 H's); 4.66–4.01 (m, 2H, 1, 3 H's); 2.93 & 2.91 (2s, each 3H, N-Me's); 0.52 (s, 3H, 18 Me). UV (Et$_2$O): $\lambda_{max}$ 270 (23,600); $\lambda_{min}$ 229 (5526).

f) 1α,3β-Dihydroxy-23,23-bishomo-24-aza-9,10-secocholesta-5(Z), 7,10(19)-trien-24-one [Formula (I) - 20R isomer, R$^1$=R$^2$=CH$_3$, R$^3$=R$^4$=H, Y=—CH$_2$CH$_2$CH$_2$CH$_2$—]

The amide from (e) above (0.072 g) was irradiated in the presence of phenazine (0.018 g) and then desilylated as described in Example 1(b) to give the title compound (0.26 g). NMR δ (CDCl$_3$): 6.33 & 5.93 (ABQ, 6, 7 H's); 5.26 & 4.93 (2, 1H, 19 H's); 4.66–3.83 (m, 2H, 1, 3 H's); 2.96 & 2.9 (2s, each 3H, N-Me's); 0.53 (s, 3H, 18 Me). UV (EtOH): $\lambda_{max}$ 264 (18,300); $\lambda_{min}$ 228 (10,892).

EXAMPLE 3 a) 1α,3β-Di(triisopropylsilyloxy)-27-nor-9,10-secocholesta-5(E),7,10(19),22,24-pentaene-26-carboxylic acid, 26 ethyl ester [5,6-trans isomer of Formula (IIIa) - X=(=CH—CH=CH—CO$_2$Et), R$^3$=R$^4$=(i-Pr)$_3$Si]

A mixture of 1α, 3β-di(triisopropylsilyloxy)-9,10-secopregna-5(E),7,10(19)-triene-20β-carboxaldehyde [5,6- trans isomer of formula (IIIa), $R_3=R_4=(i-Pr)_3Si$, $X=(=O)$] (0.452 g) and the phosphorane from 4-triphenylphosphonium-but-2-enoic acid, ethyl ester (1.2 g) in chloroform (3 ml) were refluxed for 4 hours, the solvent removed in vacuo, and the product purified by chromatography to afford the title compound (0.26 g). NMR δ ($CCl_4$): 7.26–6.41 (m, 1H, 25 H); 6.26–5.23 (m, 5H, 6,7,22,23,24 H's); 4.7 (s, 2H, 19 H's); 4.56–3.66 (m, 4H, 1,3 H's, ester $CH_2$); 0.55 (s, 3H, 18 Me). UV (EtOH): $\lambda_{max}$ 264 (39,695).

b) 1α,3β-Di(triisopropylsilyloxy)-27-nor-9,10-secocholesta-5(Z),7,10(19),22,24-pentaene-26-carboxylic acid, 26 ethyl ester [Formula (IIIa), X=(=CH—CH=CH—$CO_2Et$), $R^3=R^4=(i-Pr)_3Si$]

The ester from (a) above (0.06 g) was irradiated in the presence of phenazine (0.015 g) as described in Example 1(b) to give the title compound (0.053 g). NMR δ ($CCl_4$): 7.58–6.66 (m, 1H, 25 H); 6.41–5.33 (m, 5H, 6,7,22,23,24 H's); 5.08 & 4.75 (2s, 1H ca., 19 H's); 4.58–3.75 (m, 4H, 1,3 H's, ester $CH_2$)); 0.55 (s, 3H, 18 Me). UV (EtOH): $\lambda_{max}$ 263 (46,938).

c) 1α,3β-Dihydroxy-27-nor-9,10-secocholesta-5(Z),7,10 (19),22,24-pentaene-26-carboxylic acid, 26 dimethyl amide [Formula (I) - 20R isomer, $R^1=R^2=CH_3$, $R^3=R^4=H$, Y=—CH=CH—CH=CH—]

The ester from (b) above (0.53 g) was dissolved in a solution of 1M ethanolic potassium hydroxide (2 ml). After storage at room temperature overnight, the mixture was diluted with water, the product extracted into dichloromethane, washed with 1% aqueous sulphuric acid, and the solvent removed. The crude acid (0.046 g) was dissolved in dichloromethane (1 ml) and treated with dicyclohexylcarbodiimide (0.016 g) then dimethylamine (0.3 ml). After 30 minutes stirring at room temperature the reaction mixture was diluted with dichloromethane, the solids removed by filtration, the filtrate washed with water then with 1% aqueous sulphuric acid, and the solvent removed. Chromatography gave the 1,3-di (triisopropylsilyl ether) of the title compound (0.019 g). NMR δ ($CHCl_3$): 7.33–6.6 (m, 1H, 25 H); 6.56–5.33 (m, 5H, 6,7,22,23,24 H's); 5.06 & 4.73 (2s, 1H ea., 19 H's); 4.6–3.83 (m, 2H, 1,3 H's); 2.98 (s, 6H, NMe); 0.53 (s, 3H, 18 Me). UV (EtOH): $\lambda_{max}$ 265 (40,671). Removal of the silyl groups as described in Example 1(b) afforded the title compound (0.008 g). UV (EtOH): $\lambda_{max}$ 266 (36,775).

EXAMPLE 4 a) 1α,3β-Di(triisopropylsilyloxy)-9,10-secocholanic acid-5 (Z),7,10(19)-triene [5,6-cis isomer of Formula (IIIa) - $R^3=R^4=(i-Pr)_3Si$, $X=CH_2CO_2H$]

The ethyl ester of the title compound (prepared from the compound of Example 2(b) by photoisomerization as in Example 3(b)-140 mg) in tetrahydrofuran (0.5 ml) was treated with 1N ethanolic potassium hydroxide (3 ml). After 3 hours storage at room temperature the reaction mixture was brought to pH–2 (addition of 1% aqueous sulphuric acid) and the product extracted into ether, which was in turn washed with water and brine. Removal of the ether gave the title compound (123 mg). IR $v_{max}$ ($CCl_4$) 3200–2400 (OH of carboxyl), 1720 cm$^{-1}$ (carbonyl). NMR δ ($CCl_4$): 12.33 (1H, br, COOH); 6.03, 5.8 (2H, dd 6,7H's); 5.05, 4.75 (each 1H, s, 19H's); 5.01–4.0 (2H, m, 1,3H's); 0.53 (3H, s, 18H's). UV (EtOH): $\lambda_{max}$ 264 (18,300).

b) N,N-Pentamethylene-1α,3β-dihydroxy-9,10-secocholanamide-5(Z),7,10(19)-triene [Formula (I) - 20R isomer, $R^1+R^2=$—$(CH_2)_5$—, $R^3=R^4=H$, Y=—$(CH_2)_2$—]

The carboxylic acid from (a) above (41 mg) was dissolved in dichloromethane (0.5 ml) and treated with dicyclohexylcarbodiimide (1 eq.) and 4-dimethylaminopyridine (2 mg), and then with piperidine (1 eq.). The reaction mixture was stored overnight at room temperature. The resulting 1,3-disilylated amide was desilylated (tetrabutylammonium fluoride) as in Example 1 (b) to give the title compound. IR $v_{max}$ ($CDCl_3$) 3600 (—OH), 1630 cm$^{-1}$ (C=O, t-amide). NMR δ ($CDCl_3$): 6.26, 5.86 (2H, dd, 6,7H's); 5.2, 4.86 (each 1H, s, 19H's); 4.66–3.76 (2H, m, 1,3H's); 3.4 (4H, m, $NCH_2$); 0.5 (3H, s, 18H's). UV (EtOH): $\lambda_{max}$ 264 (18,300).

EXAMPLE 5

N-Cyclopropyl-1α,3β-dihydroxy-9,10-secocholanamide-5(Z),7,10(19)-triene [Formula (I) - 20R isomer, $R^1=H$, $R^2$=cyclopropyl, $R^3=R^4=H$, Y=—$(CH_2)_2$—]

The title compound was prepared as described in Example 4(b) using cyclopropylamine in place of piperidine. IR $v_{max}$ ($CDCl_3$) 3580 (—OH), 3420 (—NH), 1660 cm$^{-1}$ (C=O, amide). NMR δ ($CDCl_3$): 6.26, 5.83 (2H, dd, 6,7H's); 5.53 (1H, br s, NH); 5.16, 4.83 (each 1H, s, 19H's); 4.66–3.83 (2H, m, 1,3H's); 0.5 (3H, s, 18H's). UV (EtOH): $\lambda_{max}$ 265 (18,404).

EXAMPLE 6

1α,3β-Dihydroxy-9,10-secocholanamide-5(Z), 7,10(19)-triene [Formula (I) - 20R isomer, $R^1=R^2=R^3=R^4=H$, Y=—$(CH_2)_2$—]

The title compound was prepared as described in Example 4(b) using ammonia in place of piperidine. IR $v_{max}$ ($CDCl_3$) 3600 (—OH), 3525 & 3410 ($NH_2$), 1680 cm$^{-1}$ (C=O, amide). NMR δ ($CDCl_3$): 6.33, 5.91 (2H, dd, 6,7H's); 5.41 (2H, br s, NH's); 5.26, 4.91 (each 1H, s, 19H's); 4.66–3.93 (2H, m, 1,3H's); 0.53 (3H, s, 18H's). UV (EtOH): $\lambda_{max}$ 265 (18,300).

EXAMPLE 7 a) N, N-Pentamethylene-1α,3β-di(triisopropylsilyloxy)-9,10-seco-20-epi-cholanamide-5(E), 7,10(19)-triene[Formula (II) - 20S isomer, $R^1+R^2=$—$(CH_2)_5$—, $R^3=R^4=(i-Pr)_3$ Si, Y=—$(CH_2)_2$—]

The sulphur dioxide adduct of 20S-formyl-3β-triisopropylsilyloxy-9,10-secopregna-5,7,10(19)-triene (5.17 g, prepared from Vitamin $D_2$ as described in J. Org. Chem. (1986), 51, pp 4819) was converted into a ca. 1:1 mixture of 20R and 20S isomers by storage at 0° overnight in benzene (50 ml) and methanol (50 ml) containing 1,8-diazabicyclo[5.4.0.]undec-7-ene (1 ml). A portion of the mixture (2.55 g) was successively reduced with sodium borohydride, tosylated with tosyl chloride, heated in the presence of sodium bicarbonate to remove sulphur dioxide and regenerate the 5,7,10(19)-triene system, 1α-hydroxylated using selenium dioxide and methanol as described in GB-A-2038834 and silylated as described in Example 2(b) to afford a mixture (1.62 g) of the 20R (epi) and 20S (normal) isomers of the tosylate of formula (III) - $R^3=R^4=(i-Pr)_3Si$—, X=tosyloxy. A portion of this mixture (511 mg) was dissolved in acetonitrile (10 ml) and dichloromethane (10 ml), treated with lithium bromide (488 mg) and 1,8-bis(dimethylamino)naphthalene (20 mg), heated under reflux for 1.5 hours and worked up to give the bromides of formula (III), $R^3=R^4=(i-Pr)_3Si$—, X=Br, (340 mg).

A solution of N-acetylpiperidine (546 mg) in tetrahydrofuran (2 ml) was added at −78° to a solution of lithium diisopropylamide (prepared from 658 mg of diisopropylamine and 2 ml of 1.55M n-butyllithium) in tetrahydrofuran (2.5 ml). The reaction mixture was allowed to warm to room temperature, then cooled to −78°, treated with the above bromides (III) (340 mg), and stored overnight at room temperature. Workup and partial purification by chromatography gave the R, S mixture of the title compound (215 mg) and unreacted bromides (III).

An R,S mixture (300 mg) prepared as above was resolved by chromatography (20 g silica gel, developed with 5% ethyl acetate in hexane). The first isomer to emerge was the 20-epi title compound (103 mg), IR (CCl$_4$): $v_{max}$ 1645, 1465 cm$^{-1}$ (amide); UV (Et$_2$O): $\lambda_{max}$ 269, 208 nm. $\lambda_{min}$ 229 nm; NMR $\delta$ (CCl$_4$) 0.57 (3H, s, 18-H's), 3–3.5 (4H, m, N—CH$_2$), 4–4.6 (2H, m, 1,3-H's), 4.73 (2H, bs, 19-H's), 5.3–6.4 (2H, ABq, 6,7-H's). This was followed by a mixture of the epi and normal isomers (95 mg) and then the normal (20R) isomer (86 mg).

(b) N,N-Pentamethylene-1α,3β-dihydroxy-9,10-seco-20-epi-cholanamide-5(Z),7,10(19)-triene [Formula (I) - 20S isomer, R$^1$+R$^2$=—(CH$_2$)$_5$—, R$^3$=R$^4$=H, Y=—(CH$_2$)$_2$—]

Irradiation of the first fraction from (a) above in the presence of phenazine, followed by desilylation as per Example 1(b), gave the title compound, IR (CDCl$_3$): $v_{max}$ 1620, 1445 cm$^{-1}$; UV (EtOH) $\lambda_{max}$ 207, 263 nm. $\lambda_{min}$ 227 nm; NMR $\delta$ (CDCl$_3$) 0.51 (3H, s, 18-H's), 3–3.6 (4H, m, N-CH$_2$), 3.8–4.7 (2H, m, 1,3-H's), 4.7, 5.3 (1H each,s, 19-H's), 5.6–6.5 (2H, ABq, 6,7-H's) Similar treatment of the subsequent fractions gave (i) a mixture of the epi and normal isomers and (ii) the compound of Example 4(b) respectively.

We claim:

1. A method of treatment of a human or animal subject to combat neoplastic disease, bone disease, infection, autoimmune disease, host-graft reaction, transplant rejection, inflammatory disease, neoplasia, hyperplasia, acne, alopecia, psoriasis, skin aging, hypertension, rheumatoid arthritis or asthma, comprising administration to said subject of an effective amount of a compound of formula (I) or (II)

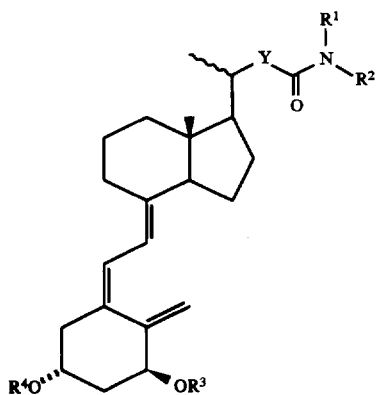

(I)

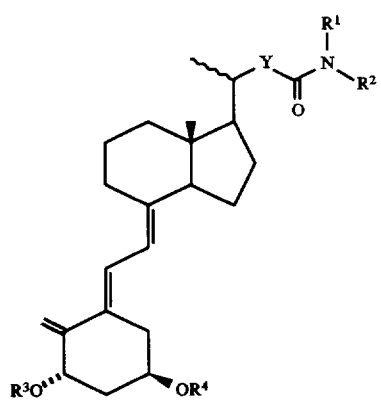

(II)

where Y represents an alkylene or alkenylene group containing up to 4 carbon atoms; R$^1$ and R$^2$, which may be the same or different, each represents a hydrogen atom or a lower alkyl or cycloalkyl group or together with the nitrogen atom to which they are attached form a heterocyclic group which is selected from the group consisting of pyrrolyl, pyrazolyl, imidazolyl, indolyl, indazolyl, purinyl, pyrrolidinyl, imidazolidinyl, pyrazolidinyl, piperidinyl, morpholino, thiazolidinyl and thiamorpholino groups; and R$^1$ and R$^4$ each represents a hydrogen atom or a metabolically labile etherifying or esterifying group.

2. The method of claim 1 wherein said neoplastic disease is myelogenous leukemia.

3. The method of claim 1 wherein said bone disease is osteoporosis.

4. The method of claim 1 wherein a compound in which Y represents a group of formula

where

R$^A$ is —CH=CH—,

R$^B$ is —CH$_2$—, m is 0, 1 or 2, and n is 0 or an integer such that 2m+n=1, 2, 3 or 4 is administered.

5. The method of claim 1 wherein a compound in which Y represents a C$_{2-4}$ alkylene group is administered.

6. The method of claim 1 wherein a compound in which at least one of R$^1$ and R$^2$ is other than hydrogen is administered.

7. The method of claim 1 wherein a compound in which R$^1$ and R$^2$ are selected from the group consisting of hydrogen atoms, methyl groups and cyclopropyl groups, or R$^1$R$^2$N— represents a piperidino group, is administered.

8. The method of claim 1 wherein a compound selected from the group consisting of 1α,3β-dihydroxy-9,10-seco-25-azacholesta-5(Z),7,10(19)-trien-24-one; 1α,3β-dihydroxy-23,23-bishomo-23-aza-9,10-secocholesta-5(Z),7,10(19)-trien-24-one; 1α,3β-dihydroxy-27-nor-9,10-secocholesta-5(Z),7,10(19),22,24-pentaene-26-carboxylic acid, 26-dimethyl amide; N,N-pentamethylene-1α,3β-dihydroxy-9-10-secocholanamide-5(Z),7,10(19)-triene; N-cyclopropyl-1α,3β-dihydroxy-9-10-secocholanamide-5 (Z),7,10(19)-triene; 1α,3β-dihydroxy-9-10-secocholanamide-5(Z),7,10(19)-triene; N,N-pentamethylene-1α,3β-dihydroxy-9,10-seco-20-epi-cholanamide-5(Z),7,10(19)-triene; and the corresponding 5(E)-isomers thereof is administered.

9. Compounds of formula (I) or (II)

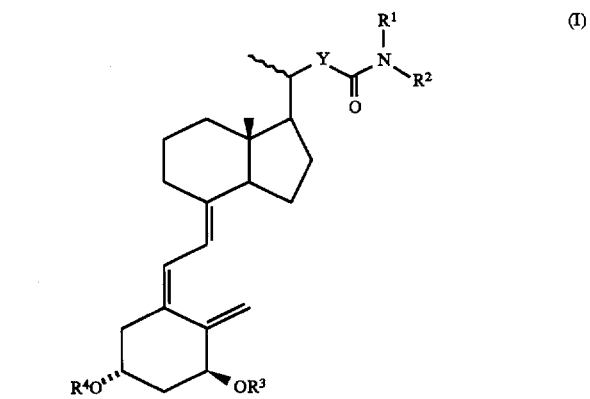

(I)

-continued

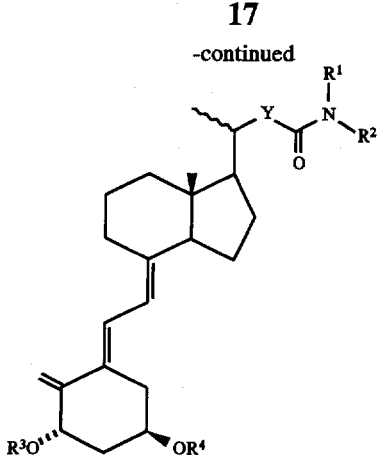

(II)

where Y represents an alkylene or alkenylene group containing up to 4 carbon atoms; $R^1R^2N-$ represents an N-attached heterocylic group which is selected from the group consisting of pyrrolyl, pyrazolyl, imidazolyl, indolyl, indazolyl, purinyl, pyrrolidinyl, imidazolidinyl, pyrazolidinyl, morpholino, thiazolidinyl and thiamorpholino groups; and $R^3$ and $R^4$ each represents a hydrogen atom or an O-protecting group.

10. Compounds as claimed in claim 9 wherein Y represents a group of formula

where
$R^A$ is $-CH=CH-$,
$R^B$ is $-CH_2-$,
m is 0, 1 or 2, and
n is 0 or an integer such that 2m+n=1, 2, 3 or 4.

11. Compounds as claimed in claim 9 wherein Y is a $C_{2-4}$ alkylene group.

12. Compounds as claimed in claim 9 wherein $R^3$ and $R^4$ represent etherifying silyl groups.

13. Compounds as claimed in claim 9 wherein $R^3$ and $R^4$ are selected from the group consisting of hydrogen atoms and metabolically labile etherifying and esterifying groups.

* * * * *